United States Patent
Smith (10) Patent No.: US 8,517,988 B2
(45) Date of Patent: Aug. 27, 2013

(54) MOTOR MECHANISM FOR A DRUG DELIVERY DEVICE AND DRUG DELIVERY DEVICE

(75) Inventor: Chrisopher James Smith, Holmes Chapel (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 29 days.

(21) Appl. No.: 13/139,923

(22) PCT Filed: Dec. 17, 2009

(86) PCT No.: PCT/EP2009/067386
§ 371 (c)(1),
(2), (4) Date: Sep. 26, 2011

(87) PCT Pub. No.: WO2010/070038
PCT Pub. Date: Jun. 24, 2010

(65) Prior Publication Data
US 2012/0010568 A1    Jan. 12, 2012

(30) Foreign Application Priority Data

Dec. 19, 2008 (EP) .................................... 08022178

(51) Int. Cl.
*A61M 5/20* (2006.01)
(52) U.S. Cl.
USPC .......................................... 604/134; 604/135
(58) Field of Classification Search
USPC ............ 604/68–72, 131, 134–136, 151–152, 604/154–157, 159, 187, 206–211
See application file for complete search history.

(56) References Cited

U.S. PATENT DOCUMENTS

| 2,956,795 A | 10/1960 | Foster |
| 4,449,543 A * | 5/1984 | Greene, Jr. .......................... 137/3 |

(Continued)

FOREIGN PATENT DOCUMENTS

| DE | 102005054313 | 5/2007 |
| EP | 1728529 | 12/2006 |

(Continued)

OTHER PUBLICATIONS

International Preliminary Report on Patentability and Written Opinion for International Patent Application. No. PCT/EP2009/067386, dated Jun. 21, 2011.

(Continued)

*Primary Examiner* — Quynh-Nhu H Vu
(74) *Attorney, Agent, or Firm* — McDonnell Boehnen Hulbert & Berghoff LLP (57) ABSTRACT

The invention refers to a motor mechanism (6) for a drug delivery device (1), comprising a storage drum (8) and a torque drum (9) arranged close to each other and a strip (7) of spring sheet metal having two ends, each end attached to one of the drums (8, 9), wherein the strip (7) of spring sheet metal is coiled on the storage drum (8) in a relaxed state, wherein the motor mechanism (6) is chargeable by rotating the torque drum (9) thereby coiling the strip (7) of spring sheet metal onto the torque drum (9) and bending the strip (7) of spring sheet metal the other way round than in the relaxed state thus arriving in a charged state with the strip (7) of spring sheet metal tending to re-coil onto the storage drum (8) thereby generating a torque.

12 Claims, 3 Drawing Sheets

(56) References Cited

U.S. PATENT DOCUMENTS

| | | | |
|---|---|---|---|
| 5,865,804 A * | 2/1999 | Bachynsky | 604/134 |
| 6,972,007 B2 * | 12/2005 | Geiser et al. | 604/211 |
| 2001/0053893 A1 | 12/2001 | Larsen | |
| 2002/0007154 A1 * | 1/2002 | Hansen et al. | 604/207 |
| 2009/0012474 A1 * | 1/2009 | Senior | 604/154 |

FOREIGN PATENT DOCUMENTS

| | | |
|---|---|---|
| WO | 02/47746 | 6/2002 |
| WO | 2006/045529 | 5/2006 |
| WO | 2006/130098 | 12/2006 |
| WO | 2007/063342 | 6/2007 |

OTHER PUBLICATIONS

International Preliminary Report on Patentability for International App. No. PCT/EP2009/067386, dated Jun. 21, 2011.
International Search Report for Int. App. No. PCT/EP2009/067386, mailed Jul. 16, 2010.
Partial European Search Report for EP Patent App. No. 08022178 dated Jul. 10, 2009.
Sharpless, E., "Designing spring-powered reels," Design Engineering, Apr. 1980, XP001028350.

* cited by examiner

MOTOR MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2009/067386 filed Dec. 17, 2009, which claims priority to EP Patent Application No. 08022178.1 filed on Dec. 19, 2008. The entire disclosure contents of these applications are herewith incorporated by reference into the present application.

FIELD OF THE INVENTION

The invention refers to a motor mechanism for a drug delivery device. The invention further refers to a drug delivery device for administering a dose of a drug. Furthermore, the invention refers to a method for generating a torque in a drug delivery device.

BACKGROUND

Injection devices (i.e. devices capable of metering and delivering a number of doses from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user—particular if the patient is elderly or has dexterity problems. The extension of the button/plunger is too great. This can be uncomfortable for the user to reach a fully extended button. The combination of injection force and button extension can cause trembling/shaking of the hand which in turn increases discomfort as the inserted needle moves.

Autoinjector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Autoinjectors require some form of energy input in order to operate. Typically this is achieved by the user performing a "priming" or "cocking" action prior to the injection. This may make the device more complicated to use, as it increases the number of user steps. Also, the actions required, for example pulling, pushing or twisting to charge a spring, may be difficult for a user to perform, particularly if the user is elderly or has dexterity problems.

In an autoinjector device—the injection of the fluid is automatic once the device has been triggered. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is typically provided by a spring which must be recharged by the user in between doses. These devices also have a number of disadvantages. Performing the "reset" action increases the number of user steps (although this can sometimes be "concealed" by making it part of the dose-selection steps). The forces required to perform the reset step may be difficult to apply—particularly for elderly or those with dexterity problems. Depending on the device the reset force may be applied as a twisting action (torque) or a push/pull.

In WO 02/47746 A1 a device for auto-injection of a dose of medicament is disclosed, comprising a housing arranged to contain a medicament container therein and comprising a contact part intended to be applied against an injection site, a needle cover surrounding a needle arranged to the medicament container and extending at least the length of the needle, spring means capable of, upon activation, pushing the needle past the end of the needle cover as well as operating said medicament container to supply the dose of medicament, first locking means capable of locking said spring means in a pressurised state, first activating means capable of, upon manual operation, releasing said spring means for injection, characterised by a second locking means capable of locking said first activating means and a second activating means, capable of releasing said second locking means when said contact part is exposed to pressure.

The spring means used in this autoinjector is a helical spring. With this spring the force from the spring is proportional to the extension of the spring. Therefore, as the spring extends and energy is released the force decreases. Multiple-dose autoinjector mechanisms using these springs must therefore be designed to be capable of delivering the final dose in the spring's extended condition. However, with the spring compressed ready to deliver the first dose the force applied may be far in excess of what is necessary. This has two consequences. Firstly, the dose delivery is variable throughout the life of the device (earlier doses are delivered with greater injection speed) and secondly some of the energy stored in the spring is "wasted" as the spring applies excessive force for many of the doses. This means that the springs may be larger than necessary and the device will have to be engineered to cope with the increased forces. The same problem applies to helical springs applying either torque or linear force or for torsional springs applying torque.

WO 2006/130098 A1 discloses a device for delivery of predetermined doses of liquid medicament. The device comprises a servo drive spring acting in the way of a clock spring for generating a torque. The torque is used for rotating a drum which advances a threaded plunger rod. The rotation of the drum may be blocked by a pin engaging with a slot when a dose of medicament has been delivered.

U.S. Pat. No. 6,972,007 B2 discloses a device for administering an injectable product in doses, the device comprising a dosing member connected to a locking means, which may be held in latching positions thus taking off a spring force onto a driven member which serves for advancing a piston and consequently for delivering a set dose of medicament. The locking means is held in the locking position by grooves engaging with corresponding protrusions.

WO 2006/045529 A1 discloses an injection device having a helical spring adapted to provide a force in the axial direction of the injection device for ejecting a dose of medicament. A rotary movement of a dose indicator barrel is caused by the force of the resilient member acting on a thread. The rotational movement may be manually blocked by appropriately switching a locking member between a locking state and an unlocking state.

WO 2007/063342 A1 discloses a pen-type injector for receiving a medication container. The injector comprises a housing and a torsion spring coupled to a drive member. A dose setting knob is coupled to the spring and rotatably coupled to a housing such that rotation of the knob in a first direction results in compression or twisting of the spring. A user actuable button is coupled to the housing for axial motion relative thereto, the button being coupled to the torsion spring to unwind or expand in discrete steps with each press of the button, which is achieved by engaging teeth of sprung legs of a clutch collet with a toothed rack.

SUMMARY

It is an object of the invention to provide a novel motor mechanism for a drug delivery device. Another object of the invention is to provide a novel drug delivery device. Yet another object of the invention is to provide a novel method for generating a torque in a drug delivery device.

The object is achieved by a motor mechanism according to claim 1, by a drug delivery device according to claim 4 and a method according to claim 16.

Preferred embodiments of the invention are given in the dependent claims.

According to the invention a motor mechanism for a drug delivery device comprises a storage drum and a torque drum arranged close to each other and a strip of spring sheet metal having two ends, each end attached to one of the drums. The strip of spring sheet metal is coiled on the storage drum in a relaxed state. The motor mechanism is chargeable by rotating the torque drum thereby coiling the strip of spring sheet metal onto the torque drum and bending the strip of spring sheet metal the other way round than in the relaxed state thus arriving in a charged state with the strip of spring sheet metal tending to re-coil onto the storage drum thereby generating a torque.

The torque is generated by a method comprising the steps of:
  providing the above motor mechanism;
  coiling the strip of spring sheet metal on the storage drum in a relaxed state;
  charging the motor mechanism by rotating the torque drum thereby coiling the strip of spring sheet metal onto the torque drum and bending the strip of spring sheet metal the other way round than in the relaxed state thus arriving in a charged state with the strip of spring sheet metal tending to re-coil onto the storage drum thereby generating the torque.

One characteristic of the inventive motor mechanism is that the torque remains relatively constant throughout the transfer of the spring from the torque drum to the storage drum. For this reason the motor mechanism may be called a constant force motor. This characteristic is particularly suitable for use in dispensing multiple doses of medication because it means that the first (with maximum stored energy in the motor mechanism) and last doses (with motor mechanism energy almost exhausted) will be delivered with very similar characteristics, such as injection speed and breakout force (this is the force required to overcome the static friction of a bung in the medication container). This means that the spring motor can be designed around one operating condition, i.e. the torque required to overcome static friction and then to deliver the medication in an appropriate injection time.

In a preferred embodiment the strip of spring sheet metal consists of spring steel.

The strip of spring sheet metal may be attached to the drums by providing a slot in the drum with the end of the strip of spring sheet metal passed through the slot.

The motor mechanism may be replaced by other "constant force" motors. Ideas for such a motor include a piston containing a compressed gas, a helical spring where energy is stored by bending the spring rather than by compression/extension and electromechanical systems (i.e. motors and batteries).

However, the spring motor mechanism is preferred for a disposable drug delivery device because it appears to be the lowest cost option whilst still fitting within the size constraints of a handheld drug delivery device. It also does not have disposability issues that may be present with electromechanical devices.

According to another aspect of the invention a drug delivery device for administering a dose of a drug comprises a container for a fluid drug and a bung for dispensing the dose. Furthermore the drug delivery device comprises a drive mechanism, at least part of it rotatable by a motor mechanism and designed to advance the bung when rotated.

The drive mechanism could also be any advancing mechanism capable of displacing drug from the drug container, for example lead-screw, rack and pinions, sliding mechanisms.

In a preferred embodiment the motor mechanism is the above described motor mechanism with the two drums and the strip of spring sheet metal. When used in an autoinjector device for automatically dispensing fluid medication from a pre-filled container containing a number of doses of medication (for example, a pre-filled syringe or a cartridge of medication) the energy to deliver all of the fluid doses may be provided during the manufacture of the device. This means that the patient does not have to provide the energy to deliver the fluid (for example by manually depressing a plunger) and the patient does not have to perform a "setting" or "cocking" action to prepare the device. A dose of medication is automatically delivered when the device is "triggered".

A latch mechanism may be provided for restricting rotation of the motor mechanism so the drug is dispensed only when required by a user. In order to prevent the drums from rotating they are held in position by the latch mechanism against the torque of the spring strip trying to return the drums to the relaxed state. The torque drum is connected to the drive mechanism. If the drums are allowed to rotate the torque created by the spring strip causes the drive mechanism to rotate, which in turn causes medication to be dispensed. The function of the latch mechanism is to control the release of the stored energy in the spring motor. The latch mechanism is designed to hold the angular position of the torque drum of the spring motor mechanism. The simplest embodiment of a latch mechanism would be for a device designed to deliver the entire contents of the drug container in a single dose. The latch mechanism would therefore hold the spring motor mechanism in its charged position and then release the spring motor mechanism when the user triggers the device.

In a preferred embodiment of the invention the latch mechanism comprises:
  a rotatable component connected to the motor mechanism and to the rotatable part of the drive mechanism;
  a cam profile on the rotatable component, the cam profile with at least one catch and at least one cam;
  a latch arm engageable with the catch for preventing rotation of the rotatable component;
  a trigger arm engageable with a protrusion of the latch arm for pivoting the latch arm out of the catch by translative movement of the trigger arm thus allowing rotation of the rotatable component, the trigger arm pivotable by the cam during the rotation of the rotatable component for disengaging the trigger arm from the protrusion.

The latch mechanism allows for restricting the rotational movement of the rotatable component until the latch arm re-engages with the catch, so it is suited for a multi-dose drug delivery device. Each time the user triggers the dispense mechanism the latch mechanism is temporarily disengaged allowing the torque drum to rotate under the action of the coiled strip of spring sheet metal. The latch engages again after the desired rotation of the torque drum to achieve the required dose. This happens after one full 360° rotation when only one catch is provided in the cam profile or after a fraction of a full rotation when more than one catch is provided.

In a particularly preferred embodiment the latch mechanism further comprises:

an interlocking means for catching and holding the trigger arm once the trigger arm has been translatively moved and pivoted;

reset means for releasing the trigger arm from the interlocking means.

The interlocking means is not a requirement of the latch mechanism. However, it offers a significant safety advantage for the drug delivery device. With the interlocking means another rotation cannot be triggered unless the interlocking means releases the trigger arm. This can be performed by some kind of user action to ensure that the triggering is intentional. The interlock means may be applied for ensuring that only one dose of the drug is delivered at a time in a multi-dose drug delivery device with each full or partial rotation of the rotatable component. Thus a user is prevented from administering multiple doses, e.g. by pressing a trigger button more than once or by holding the trigger button pressed whilst a needle is inserted into his body. Before a second injection can be triggered the user must perform some action that preferably cannot take place without first removing the needle from the body. Therefore, it is highly unlikely that the user could accidentally reset the interlock mechanism whilst the needle is inserted into the body.

The latch mechanism is particularly suited to delivery of fixed doses of medication from the drug container since a fixed-dose device does not require a "dose-selection" step and therefore providing the dispensing energy during manufacture reduces the number of user steps to a minimum. However, the mechanism could also be adapted to deliver variable doses of medication (for example a dial-up insulin delivery device).

The reset means for releasing the interlock means may be operated manually by operating a lever or the like. Preferably the reset means is automatically operated. For example the interlock means may be released when a safety cap is placed on the drug delivery device or when a needle of a syringe contained in the drug delivery device is changed, in particular when the interlock mechanism is used in multi-dose drug delivery devices for preventing it to deliver more than one dose at a time. The reset means may also be released when an injection site is contacted with the drug delivery device or the drug delivery device is pressed against the injection site, e.g. the user's skin.

In another embodiment the reset means may be operated when the safety cap is removed from the drug delivery device. This is particularly useful when the interlock mechanism is used for preventing accidental triggering of the drug delivery device, e.g. when carrying the device around in a bag.

When the interlocking mechanism is used in a one-shot drug delivery device the dose delivered during one rotation of the rotatable component may equal at least almost a total volume of the drug held in the syringe contained in the drug delivery device.

The drug delivery device may have a needle for delivering the drug through or into the skin. Alternatively the drug delivery device may be a jet injector with a jet nozzle for needle free injections. The drug delivery device may also be a dose inhaler device.

The drive mechanism for converting the rotational movement of the motor mechanism into a translative movement of the bung may comprise a telescopic piston with a driver and a plunger telescoped one into the other and connected to each other by a screw thread. The driver is connected to the motor mechanism; the plunger is prevented from rotating and connected to the bung. The plunger may screw over an outside of the driver or vice versa. Initially, the driver and plunger overlap along a significant portion of their length. When the driver rotates the plunger is prevented from rotating, for example by means of a slot or the geometry of its external form. The screw thread between the driver and the plunger causes the plunger to advance forwards, thus the combined length of driver and plunger is extended. A pitch of the screw thread may be designed such that the degree of extension of the telescopic piston is equal to the required displacement of the "bung" of the drug container in order to dispense the required dose.

The telescopic piston may also comprise more than two parts telescoped one in another. Also, a single fixed piston is possible if the autoinjector mechanism is permitted to move along the drug delivery device with the piston as the piston advances.

In an alternative embodiment the motor mechanism may comprise a piston driven by compressed gas or a helical spring or an electric motor with a battery.

In order to allow the user to reuse the drug delivery device manual means for recharging the motor mechanism may be provided, e.g. by rewinding the strip of spring sheet metal onto the torque drum.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given herein below and the accompanying drawings which are given by way of illustration only, and thus, are not limited of the present invention, and wherein.

DETAILED DESCRIPTION

Figure 1:
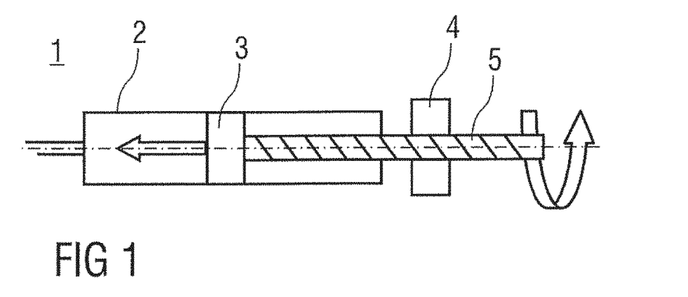
FIG. 1 is a schematic lateral view of a drug delivery device.

FIG. 1 shows a drug delivery device 1, comprising a container 2 for a fluid drug and a bung 3 for dispensing the dose, further comprising a drive mechanism with telescopic piston comprising a driver 4 and a plunger 5 telescoped one in the other and connected to each other by a screw thread. The driver 4 may be rotated by a motor mechanism (not shown) while the plunger 5 is prevented from rotating, for example by means of a slot or the geometry of its external form. Thus, when the driver 4 is rotated the plunger 5 and the bung 3 are advanced and hence a dose of drug is dispensed from the container 2. The bung 3 does not necessarily have to be directly connected to the plunger 5.

Figure 2A:
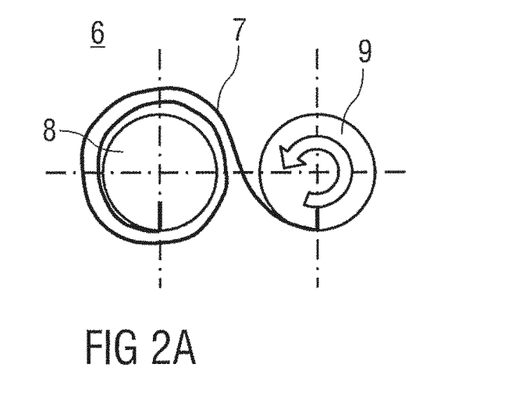
FIG. 2A, 2B show a schematic view of a motor mechanism for the drug delivery device.

FIG. 2A shows a schematic view of a motor mechanism 6 for the drug delivery device 1 in a relaxed state. The motor mechanism 6 contains a strip 7 of spring sheet metal, e.g. made of spring steel. Two drums are provided—a storage drum 8 and a torque drum 9. The coiled flat spring strip 7 is assembled over the storage drum 8 and one end of the flat spring strip 7 that is on the inside of the coil is connected to the storage drum 8, for example by passing the end of the strip 7 through a slot (not shown) in the storage drum 8. The torque drum 9 is assembled close to the storage drum 8 and the outside end of the flat spring strip 7 is connected to the torque drum 9, for example by passing the end of the strip 7 through a slot (not shown) in the torque drum 9.

Figure 2B:
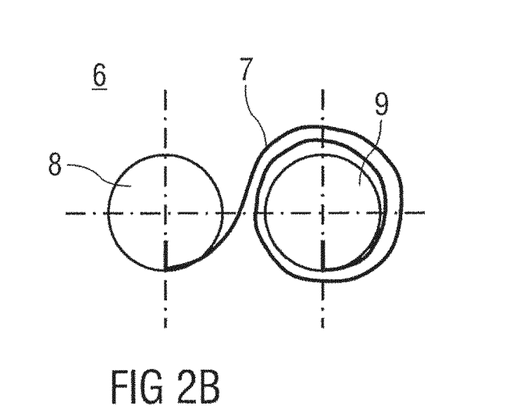

FIG. 2B shows the motor mechanism 6 in a charged state. The motor mechanism 6 is charged by rotating the torque drum 9. This may be done by manually rotating a spring reset dial. Typically in manufacture of a disposable drug delivery device 1 this would rather be done during production of the device in the factory with no manual dial in the device 1. The strip 7 is unwound from the storage drum 8 and wound back on itself in a figure-of-eight fashion to create a coil on the torque 9 drum. Thereby the strip 7 of spring sheet metal is bent the other way round than in the relaxed state thus arriving in the charged state with the strip 7 of spring sheet metal tending to re-coil onto the storage drum 8. If the drums 8, 9 are released at this point the strip 7 tends to return to its original relaxed state on the storage drum 8 and thus causes both drums 8, 9 to rotate until the strip 7 is completely transferred back onto the storage drum 8.

FIG. 3A to 3F show a latch mechanism 10 of the drug delivery device 1 for controlling rotation R of a rotatable component 11 connected to the motor mechanism 6. The embodiment shown is intended to be applied as a multiple-dose latch mechanism 10. In this embodiment one dose of drug is delivered by one full rotation of the rotatable component 11.

The latch mechanism 10 comprises:
  a cam profile on the rotatable component 11, the cam profile having a catch 13 and a cam 14;
  a swivel mounted latch arm 15 engageable with the catch 13 for preventing rotation R of the rotatable component 11;
  a swivel mounted and translatively moveable trigger arm 16 engageable with a protrusion 17 of the latch arm 15 for pivoting the latch arm 15 out of the catch 13 by translatively movement T of the trigger arm 16 thus allowing rotation R of the rotatable component 11, the trigger arm 16 pivotable by the cam 14 during the subsequent rotation R of the rotatable component 11 for disengaging the trigger arm 16 from the protrusion 17;
  an interlocking means 18 for catching and holding the trigger arm 16 once the trigger arm 16 has been translatively moved and pivoted;
  reset means (not shown) for releasing the trigger arm 16 from the interlocking means 18.

Figure 3A:
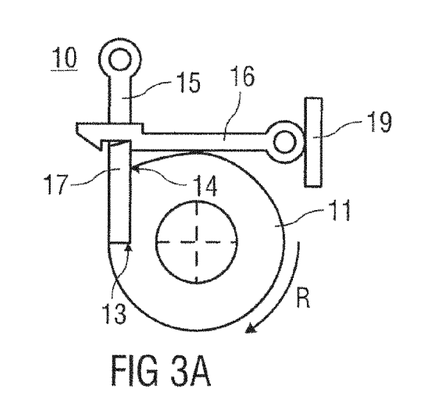
FIG. 3A to 3F show a latch mechanism for controlling rotation of rotatable components of the drug delivery device.

In FIG. 3A the latch mechanism 10 is in an initial state ready for triggering. The latch arm 15 is engaged with the catch 13 thus preventing rotation R of the rotatable component 11. The trigger arm 16 is in an initial position engaged with the protrusion 17 of the latch arm 15.

Figure 3B:
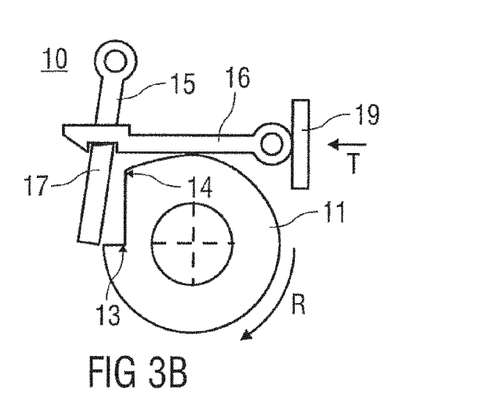
Figure 3C:
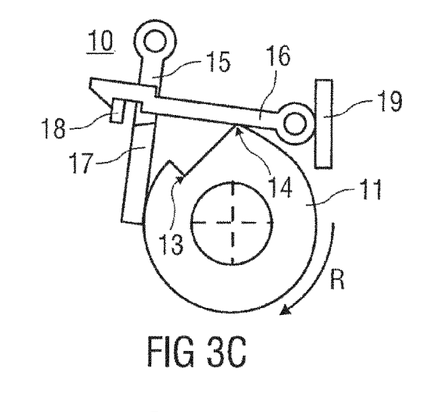

In FIG. 3B a trigger button 19 is pushed thereby translatively moving the trigger arm 16 out of its initial position. The trigger arm 16 engaged with the protrusion 17 of the latch arm 15 pivots the latch arm 15 out of the catch 13. The rotatable component 11, biased by an energy source, such as the motor mechanism 6 now starts rotating as shown in FIG. 3C.

During the start of the rotation R of the rotatable component 11 the trigger arm 16 is pivoted by the cam 14. Thereby the trigger arm 16 is disengaged from the protrusion 17 thus allowing the latch arm 15 to re-engage with the catch 13 after a full 360° rotation R. Also by pivoting the trigger arm 16 the interlock means 18, e.g. under tension of a spring catches and holds the trigger arm 16 in its translatively moved and pivoted position. The figures show the trigger arm 16 being held by the interlock means 18 in a kind of hook. Alternatively there could be a recess in the trigger arm 16 for engaging with the interlock means 18.

Figure 3D:
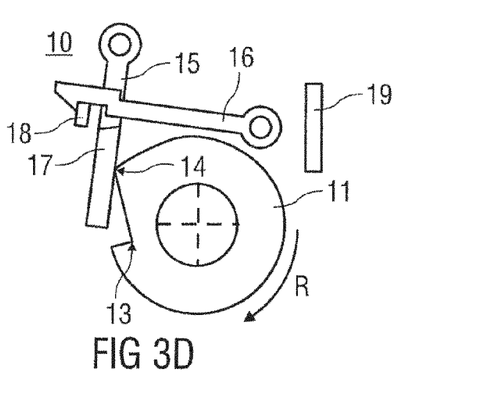

In FIG. 3D the 360° rotation R is almost complete. The trigger button 19 was released by the user and is returned to its initial position, e.g. by means of a spring. Pressing it again does not have an effect since the trigger arm 16 is decoupled from the trigger button 19.

Figure 3E:
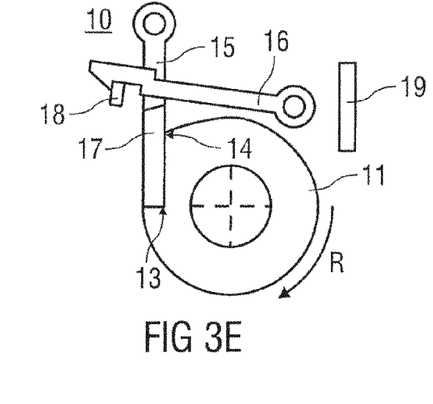

In FIG. 3E the 360° rotation R is complete. The latch arm 15, e.g. biased by a spring is re-engaged with the catch 13 thus preventing further rotation. The trigger arm 16 is still held by the interlock means 18 so the rotatable component 11 cannot be triggered.

Figure 3F:
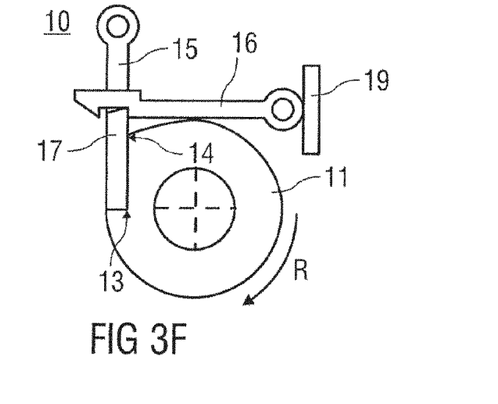

In FIG. 3F the interlock means 18 has been released by some kind of user action. The trigger arm 16, e.g. biased by a spring, is now free to return to its initial position and to re-engage with the protrusion 17 to allow another trigger cycle.

The interlock means 18 may be reset by means of a manual button. However, it is preferred that this could be accomplished "automatically" by the user upon replacing a device cap or changing a needle. For example, attaching the device cap might displace a rod that is connected directly to the interlock means 18.

The reset means for releasing the interlock means 18 may be operated manually by operating a lever or the like. Preferably the reset means is automatically operated. For example the interlock means 18 may be released when a safety cap is placed on the drug delivery device 1 or when a needle of the drug container 2 is changed. The reset means may also be released when an injection site is contacted with the drug delivery device 1 or the drug delivery device 1 is pressed against the injection site, e.g. the user's skin.

In another embodiment the reset means may be operated when the safety cap is removed from the drug delivery device 1.

When the latch mechanism 10 is used in a one-shot drug delivery device 1 the dose delivered during one rotation R of the rotatable component 11 may equal at least almost a total volume of the drug held in the drug container 2.

The drug delivery device 1 may have a needle for delivering the drug through or into the skin. Alternatively the drug delivery device 1 may be a jet injector with a jet nozzle for needle free injections. The drug delivery device 1 may also be a dose inhaler device.

The drug delivery device 1 may be a fixed-dose delivery device where the device contains a number of fixed doses. It may also be a variable dose device.

The embodiment shown is intended for preventing a user from accidentally triggering the drug delivery device 1 more than once.

Alternatively the latch mechanism 10 could be applied for accidentally triggering the drug delivery device 1 at all. This latch mechanism 10 could work by disengaging the trigger button 19 from the dispensing mechanism. This could be accomplished in a similar manner to the multiple-dose latch mechanism 10 by detecting the presence of the device cap.

The same component that detects the device cap, and connects to the multiple-dose interlock reset, could also form a key link between the external trigger button 19 and the dispensing mechanism trigger. When the cap is present this link feature would be displaced out of the chain between external trigger button 19 and internal mechanism trigger. When the cap is removed the link feature would move into position between the external trigger button 19 and mechanism trigger such that movement of the trigger button 19 is transferred via the link feature to the mechanism trigger.

An alternative embodiment for the accidental-dose interlock would be for the cap of the device to physically prevent the trigger button 19 from being pressed.

The cam profile of the rotatable component 11 may have more than one catch 13 and more than one cam 14. In this case the rotation R stops the re-engaging latch arm 15 and catch 13 after a fraction of a 360° rotation.

The interlocking means 18 is not a requirement of the latch mechanism 10.

Figure 4:
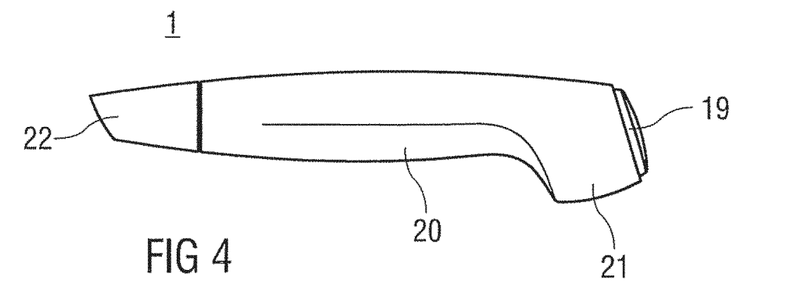
FIG. 4 shows a lateral view of the drug delivery device.

FIG. 4 shows a view of a possible embodiment of the drug delivery device 1, comprising a body 20 surrounding the components described in the FIGS. 1 to 3. At a back end of the body 20 a widened portion 21 is provided for housing the motor mechanism 6 with the two drums 8, 9 arranged side by side. The trigger button 19 is also arranged at the back end. At the opposite front end a device cap 22 is provided for securing the needle against accidentally being touched by the user.

The drug container 2 shown in the embodiments has a cylindrical body and a slidable rubber bung 3 upon which the device mechanism acts. However, alternative drug containers 2 would also be possible including different shapes and sizes of container 2, containers 2 where the rubber bung 3 is directly connected to part of the device mechanism (i.e. the plunger 5 part of the piston also forms the container bung 3), collapsible medication pouches or pre-measured dosage formats including blister packs or containers 2 with individual capsules or medication.

Alternative latching mechanisms 10 are also possible. This could include a device that could deliver variable sized doses, either automatically (for example a dose that gradually increments over the course of the treatment) or manually (for example a device where the patient selects their dose by turning a dial).

The invention claimed is:

1. A motor mechanism for a drug delivery device, comprising a storage drum and a torque drum arranged close to each other and a strip of spring sheet metal having two ends, each end attached to one of the drums, wherein the strip of spring sheet metal is coiled on the storage drum in a relaxed state, wherein the motor mechanism is chargeable by rotating the torque drum thereby coiling the strip of spring sheet metal onto the torque drum and bending the strip of spring sheet metal the other way round than in the relaxed state thus arriving in a charged state with the strip of spring sheet metal tending to re-coil onto the storage drum thereby generating a torque.

2. The motor mechanism according to claim 1, characterized in that the strip of spring sheet metal consists of spring steel.

3. The motor mechanism according to claim 1, characterized in that a slot is provided in the drum with the end of the strip of spring sheet metal passed through the slot.

4. A drug delivery device for administering a dose of a drug, the drug delivery device comprising a container for a fluid drug and a bung for dispensing the dose, further comprising a drive mechanism, at least part of it rotatable by a motor mechanism thereby advancing the bung, wherein the motor mechanism comprises a storage drum and a torque drum arranged close to each other and a strip of spring sheet metal having two ends, each end attached to one of the drums, wherein the strip of spring sheet metal is coiled on the storage drum in a relaxed state, wherein the motor mechanism is chargeable by rotating the torque drum thereby coiling the strip of spring sheet metal onto the torque drum and bending the strip of spring sheet metal the other way round than in the relaxed state thus arriving in a charged state with the strip of spring sheet metal tending to re-coil onto the storage drum thereby generating a torque.

5. A drug delivery device according to claim 4, characterized in that a latch mechanism is configured to restrict rotation (R) of the motor mechanism.

6. A drug delivery device according to claim 5, characterized in that the latch mechanism comprises:

a rotatable component connected to the motor mechanism and to the rotatable part of the drive mechanism;

a cam profile on the rotatable component, the cam profile with at least one catch and at least one cam;

a latch arm engageable with the catch for preventing rotation (R) of the rotatable component; and a trigger arm engageable with a protrusion of the latch arm for pivoting the latch arm out of the catch by translative movement (T) of the trigger arm thus allowing rotation (R) of the rotatable component, the trigger arm pivotable by the cam during the rotation (R) of the rotatable component for disengaging the trigger arm from the protrusion;

wherein the latch mechanism prevents the storage drum and torque drum from rotating.

7. A drug delivery device according to claim 6, characterized in that the latch mechanism further comprises:

an interlock configured to releasably catch and hold the trigger arm once the trigger arm has been translatively moved and pivoted.

8. A drug delivery device according to claim 6, characterized in that the trigger arm is configured to be released from the interlock by placing or removing a safety cap on the drug delivery device or by changing a needle of a syringe contained in the drug delivery device or by contacting an injection site with the drug delivery device.

9. A drug delivery device according to claim 4, characterized in that a needle or a jet nozzle is provided for administering the drug into or through a human's or animal's skin.

10. A drug delivery device according to claim 4, characterized in that the drive mechanism comprises a driver and a plunger connected to each other by a screw thread, the driver connected to the motor mechanism, the plunger prevented from rotating and abutting the bung.

11. A drug delivery device according to claim 4, characterized in that the motor mechanism is configured to be manually recharged by a user of the drug delivery device.

12. A method for generating a torque in a drug delivery device, wherein the torque is convertible into a translative force acting on a bung for dispensing a fluid drug from a container arranged in the drug delivery device, the method comprising the steps of:

providing a motor mechanism comprising a storage drum and a torque drum arranged close to each other and a strip of spring sheet metal having two ends, each end attached to one of the drums;

coiling the strip of spring sheet metal on the storage drum in a relaxed state;

charging the motor mechanism by rotating the torque drum thereby coiling the strip of spring sheet metal onto the torque drum and bending the strip of spring sheet metal the other way round than in the relaxed state thus arriving in a charged state with the strip of spring sheet metal tending to re-coil onto the storage drum thereby generating the torque.

* * * * *

UNITED STATES PATENT AND TRADEMARK OFFICE
CERTIFICATE OF CORRECTION

PATENT NO. : 8,517,988 B2  
APPLICATION NO. : 13/139923  
DATED : August 27, 2013  
INVENTOR(S) : Chrisopher James Smith Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 129 days.

Signed and Sealed this

Fifteenth Day of September, 2015

Michelle K. Lee
*Director of the United States Patent and Trademark Office*